(12) United States Patent
Tanigaki (10) Patent No.: US 10,434,289 B2
(45) Date of Patent: Oct. 8, 2019

(54) GUIDE WIRE

(71) Applicant: TERUMO KABUSHIKI KAISHA, Shibuya-ku, Tokyo (JP)

(72) Inventor: Nobuyuki Tanigaki, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/652,933

(22) Filed: Jul. 18, 2017

(65) Prior Publication Data

US 2017/0312483 A1 Nov. 2, 2017

Related U.S. Application Data

(63) Continuation of application No. PCT/JP2015/084748, filed on Dec. 11, 2015.

(30) Foreign Application Priority Data

Jan. 23, 2015 (JP) .................................. 2015-011817

(51) Int. Cl.
*A61M 25/09* (2006.01)
*A61M 25/10* (2013.01)
*A61M 39/06* (2006.01)

(52) U.S. Cl.
CPC ............ *A61M 25/09* (2013.01); *A61M 25/10* (2013.01); *A61M 39/06* (2013.01); *A61M 2025/09175* (2013.01); *A61M 2039/0626* (2013.01)

(58) Field of Classification Search
CPC ............ A61M 25/09; A61M 2039/062; A61M 25/0082; A61M 25/065; A61B 18/1492; A61B 5/6852

USPC .......................... 600/585, 435, 479; 606/158
See application file for complete search history.

(56) References Cited

U.S. PATENT DOCUMENTS 5,167,239 A * 12/1992 Cohen .............. A61B 17/22032
600/434
5,722,963 A * 3/1998 Lurie ................. A61M 25/0041
600/585
6,004,279 A * 12/1999 Crowley ............... A61M 25/09
600/433

(Continued)

FOREIGN PATENT DOCUMENTS

JP 2007-044388 A 2/2007
JP 2009-045464 A 3/2009
JP 2013-085781 A 5/2013

OTHER PUBLICATIONS

International Search Report (PCT/ISA/210) dated Mar. 8, 2016, by the Japanese Patent Office as the International Searching Authority for International Application No. PCT/JP2015/084748.

*Primary Examiner* — May A Abouelela
(74) *Attorney, Agent, or Firm* — Buchanan Ingersoll & Rooney PC (57) ABSTRACT

A guide wire capable of exhibiting improved penetrability for penetrating a stenosis without degradation of passing performance of the guide wire. A guide wire includes a wire main body formed into a linear shape, a distal end portion of the wire main body is formed into a curved shape by a top portion that forms an extreme distal portion and a surrounding portion that makes the top portion continuous with a peripheral surface of the wire main body, a plurality of recesses are formed in the distal end portion, and the recesses are formed in the top portion and the surrounding portion, respectively.

17 Claims, 7 Drawing Sheets

(56) References Cited

U.S. PATENT DOCUMENTS

| | | | | |
|---|---|---|---|---|
| 6,607,496 B1* | 8/2003 | Poor | | A61M 25/0012 600/585 |
| 8,246,574 B2* | 8/2012 | Jacobs | | A61M 25/0053 600/585 |
| 2002/0143251 A1* | 10/2002 | Richardson | | A61M 25/0023 600/434 |
| 2003/0069522 A1* | 4/2003 | Jacobsen | | A61M 25/0013 600/585 |
| 2003/0078519 A1* | 4/2003 | Salahieh | | A61F 2/013 600/585 |
| 2003/0093029 A1* | 5/2003 | McGuckin, Jr. | | A61M 1/285 604/43 |
| 2006/0009715 A1* | 1/2006 | Khairkhahan | | A61B 5/0084 600/585 |
| 2007/0100285 A1* | 5/2007 | Griffin | | A61M 25/0013 604/164.11 |
| 2009/0054921 A1 | 2/2009 | Yanuma | | |
| 2010/0222637 A1* | 9/2010 | Kassab | | A61B 5/02152 600/17 |
| 2010/0234698 A1* | 9/2010 | Manstrom | | A61M 5/007 600/301 |
| 2010/0286718 A1* | 11/2010 | Kassab | | A61B 17/00491 606/158 |
| 2010/0305475 A1* | 12/2010 | Hinchliffe | | A61M 25/09 600/585 |
| 2012/0041308 A1 | 2/2012 | Yanuma | | |
| 2012/0203163 A1* | 8/2012 | Thomas | | A61B 17/320758 604/22 |
| 2012/0277725 A1* | 11/2012 | Kassab | | A61B 17/00491 604/508 |
| 2013/0096455 A1* | 4/2013 | Kassab | | H01B 7/048 600/547 |
| 2013/0345709 A1* | 12/2013 | Burger | | A61B 17/8811 606/94 |
| 2014/0018831 A1* | 1/2014 | Kassab | | A61B 17/12122 606/158 |
| 2014/0163384 A1* | 6/2014 | Torrance | | A61B 17/3207 600/471 |
| 2014/0276117 A1* | 9/2014 | Burkett | | A61B 5/6852 600/479 |
| 2014/0330211 A1* | 11/2014 | Kassab | | A61B 17/00491 604/176 |
| 2015/0005595 A1* | 1/2015 | Tepper | | A61K 9/0097 600/309 |
| 2015/0272615 A1* | 10/2015 | Newhauser | | A61B 17/320758 606/159 |
| 2016/0113582 A1* | 4/2016 | Altmann | | A61B 5/6858 600/374 |

* cited by examiner

FIG. 1

(Prior Art)

GUIDE WIRE

CROSS-REFERENCE TO RELATED APPLICATIONS

This application is a continuation of International Application No. PCT/JP2015/084748 filed on Dec. 11, 2015, which claims priority to Japanese Application Number 2015-011817 filed on Jan. 23, 2015, the entire contents of which are incorporated herein by reference.

TECHNICAL FIELD

The disclosure herein relates to a medical guide wire.

DESCRIPTION

When a catheter is inserted into a body lumen, a guide wire is used to guide the catheter to a region of interest in the body lumen. The guide wire is formed to be insertable into the catheter along an axial direction thereof, is inserted into the body lumen prior to the catheter, and guides insertion of the catheter. The guide wire is also used to guide an endoscope.

The guide wire, which is used in a catheter for treatment of a stenosis of a blood vessel, is required to have excellent penetrability for approaching the stenosis of the blood vessel. Particularly in a case where the blood vessel has severe stenosis such as chronic total occlusion, it is necessary to improve the penetrability of the guide wire because a distal end portion of the guide wire slipping on a surface of the stenosis makes it difficult for the distal end portion to approach the stenosis.

To improve the penetrability of the guide wire, there is known a technique, as disclosed in, for example, JP-A-2013-85781, for providing a tip having a tapered portion narrower in diameter toward a distal end of the tip in the distal end portion of the guide wire, and forming the distal end of the tip into a circular arc shape.

When the blood vessel has severe stenosis and particularly when the blood vessel is completely blocked, there is a probability that sufficient penetrability cannot be ensured even for the guide wire contrived as described above. This is because the distal end portion of the guide wire slips on the surface of the stenosis and is not caught on the surface of the stenosis. Furthermore, manipulation time is often prolonged because the penetrability of the guide wire cannot be sufficiently ensured to make it difficult for the guide wire to approach the stenosis.

JP-A-2013-85781 also discloses a technique for providing a plane section on the distal end of the guide wire and forming a recess in the plane section, thereby improving the penetrability. In this case, however, the plane section is facing a direction of forward movement of the guide wire and comes into surface contact with an interior of the body lumen. As a result, the passing performance of the guide wire within the body lumen may be degraded.

SUMMARY

The disclosure herein provides a guide wire capable of exhibiting improved penetrability for penetrating a stenosis without degradation of passing performance of the guide wire.

A guide wire according to an exemplary embodiment of the disclosure here includes a wire main body formed into a linear shape, wherein a distal end portion of the wire main body is formed into a curved shape by a top portion that forms an extreme distal portion and a surrounding portion that makes the top portion continuous with a peripheral surface of the wire main body, and a plurality of recesses are formed in the distal end portion.

The guide wire configured as described above can suppress the slipping of the distal end portion on a stenosis due to the presence of the recesses and thus improve the penetrability of the guide wire while also improving the passing performance of the guide wire within the body lumen due to the curved distal end portion.

Forming the recesses in the top portion and the surrounding portion, respectively can suppress the slipping even when the distal end portion of the guide wire does not move straight into the stenosis.

Forming the plurality of recesses along the circumferential direction of the surrounding portion can suppress the slipping on the stenosis irrespective of the circumferential orientation of the guide wire.

Making the recesses formed in the surrounding portion identical in shape and disposing the recesses equidistantly along the circumferential direction can constantly suppress slipping on the stenosis irrespective of the circumferential orientation of the guide wire.

Forming a plurality of rows of the recesses along an axial direction of the surrounding portion can suppress the slipping of the distal end portion on the stenosis in a wider range.

Forming a circular distal recess in the top portion and forming circular or oval surrounding recesses in the surrounding portion can ensure suppression of the slipping because the edge of the distal recess or each surrounding recess is caught on the stenosis at whichever angle the guide wire comes in contact with the stenosis.

Configuring the surrounding recess to be oval and disposing the surrounding recess such that a long axis faces along the circumferential direction of the surrounding portion and a short axis faces along the axial direction of the surrounding portion can elongate the edge of each surrounding recess in a direction orthogonal to a slipping direction and increase a resistance force against the slipping when the distal end portion of the guide wire slips against an axial force.

DETAILED DESCRIPTION

Exemplary embodiments of the disclosure herein will be described hereinafter with reference to the drawings. It is noted that a scale ratio of the drawings is exaggerated for the convenience of description and often differs from an actual scale ratio. In the present description of the disclosure, a side of a catheter 10 inserted into a body lumen will be referred to as "distal end" or "distal side" while a handling hand side thereof will be referred to as "proximal end" or "proximal side". Furthermore, each figure schematically shows a guide wire 1 while a length direction thereof is reduced and a thickness direction thereof is exaggerated, so that a ratio of the length direction to the thickness direction differs from an actual ratio.

Figure 1:
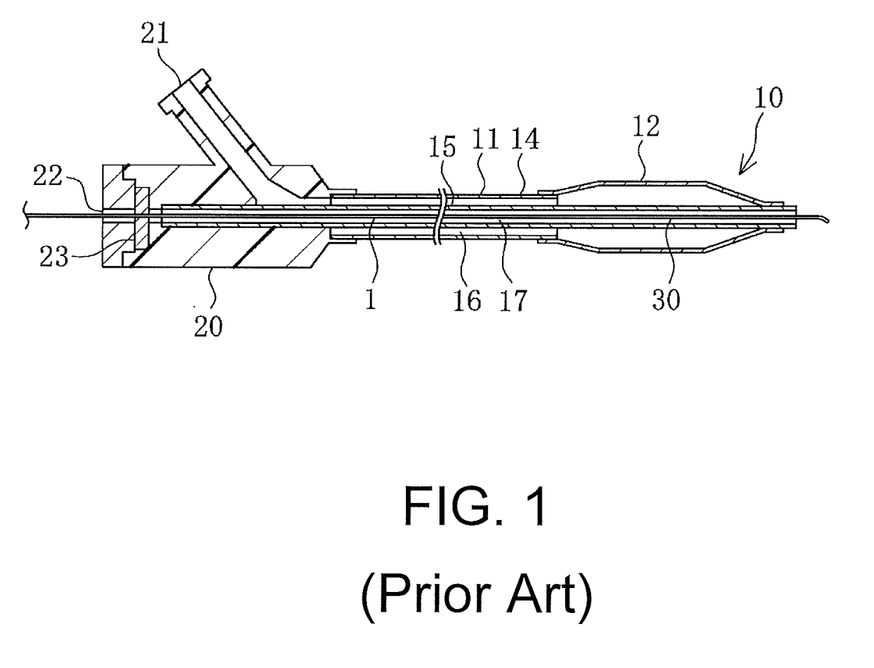
FIG. 1 is a cross-sectional view illustrating the entire structure of a conventional catheter for which a guide wire is used.

First, a configuration of the catheter 10 using the guide wire 1 according to an exemplary embodiment will be described. As shown in FIG. 1, the catheter 10 using the guide wire 1 according to the exemplary embodiment includes an elongated and hollow catheter main body portion 11, a balloon 12 provided on a distal end portion of the catheter main body portion 11, and a hub 20 fixedly bonded to a proximal end of the catheter main body portion 11.

The catheter main body portion 11 includes an outer tube 14 that is a hollow tube-shaped body and an inner tube 15 that is a hollow tube-shaped body disposed within the outer tube 14. A dilation lumen 16 in which a dilation fluid for dilating the balloon 12 circulates is formed between the outer tube 14 and the inner tube 15, and a guide wire lumen 17 into which the guide wire 1 is inserted is formed inside the inner tube 15.

Preferably, the outer tube 14 and the inner tube 15 are each formed from a material exhibiting a certain degree of flexibility. Examples of such a material to be used include polyolefin such as polyethylene, polypropylene, polybutene, ethylene-propylene copolymer, ethylene-vinyl acetate copolymer, ionomer, and mixtures of two or more types of the above polymers, fluorocarbon resin such as soft polyvinyl chloride resin, polyamide, polyamide elastomer, polyester, polyester elastomer, polyurethane, and polytetrafluoroethylene, silicone rubber, and latex.

A distal side of the balloon 12 is adhesively bonded to the inner tube 15, a proximal side thereof is adhesively bonded to the outer tube 14, and an interior of the balloon 12 is in communication with the dilation lumen 16. It is thereby possible to dilate the balloon 12 by injecting the dilation fluid into the balloon 12 via the dilation lumen 16. The dilation fluid may be either a gas or a liquid, using a gas such as helium gas, $CO_2$ gas, or $O_2$ gas, or a liquid such as a saline solution or a contrast agent can be used as the dilation fluid.

The hub 20 includes a first opening portion 21 that functions as a port which communicates with the dilation lumen 16 formed between the outer tube 14 and the inner tube 15 and into or out of which the dilation fluid flows, and a second opening portion 22 that communicates with the guide wire lumen 17. A hemostasis valve 23 inhibiting outflow of blood while the guide wire 1 is allowed to be freely inserted into the hemostasis valve 23 is provided in the second opening portion 22.

During a treatment, the guide wire 1 is inserted into the catheter 10 from the second opening portion 22 up to a distal end of the catheter main body portion 11 through the guide wire lumen 17. Furthermore, a distal end of the guide wire 1 protrudes further to a distal side than the distal end of the catheter main body portion 11. It is noted that the distal end of the guide wire 1 and a vicinity of the distal end thereof are slightly curved. During manipulation, the catheter main body portion 11 is inserted into the body lumen while the guide wire 1 is inserted thereinto earlier than the catheter main body portion 11.

The guide wire 1 according to the first exemplary embodiment will be described in detail. The guide wire 1 includes a wire main body 30 formed into an elongated linear shape. The wire main body 30 is an elastic wire rod and formed by winding a wire around a core wire. The core wire and the wire are formed from a metal material such as stainless steel. It is noted that the wire main body 30 may be formed from resin.

An entire length of the guide wire 1 is, in general, but not exclusively, about 200 to 5000 mm. Similarly, an outer diameter of the core wire is preferably, but not exclusively, in a range from 0.03 to 0.5 mm. Similarly, an outer diameter of the guide wire 1 is, in general, but not exclusively, about 0.2 to 1.2 mm. In the first exemplary embodiment, a load acting on the distal end of the guide wire 1 is in a range from 0.3 to 80 gf.

Figure 2:
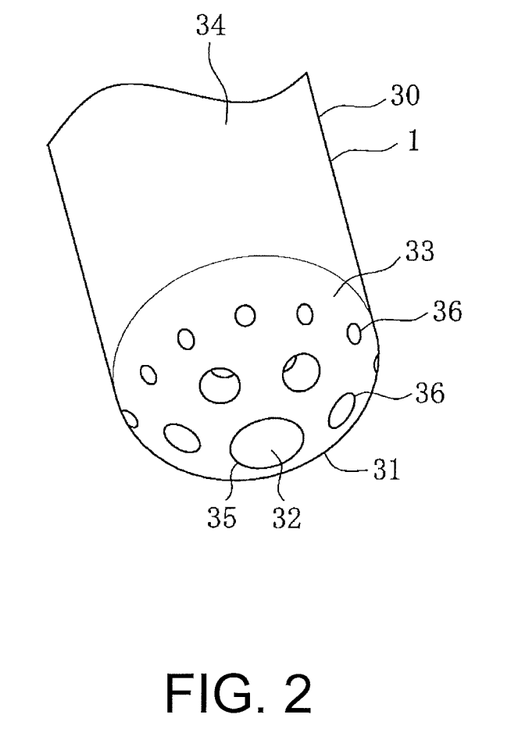
FIG. 2 is a perspective view of a distal end portion of a guide wire according to a first exemplary embodiment of the disclosure.

No wire is wound around a distal end portion 31 of the wire main body 30 but a tip is provided on the distal end portion 31. The tip is formed from a solder, silver, gold, or the like, or is formed from resin when the wire main body 30 is formed from resin. Preferably, a diameter of the tip is in a range from 0.2 to 0.8 mm and a length of the tip is in a range from 0.05 to 10 mm. This distal end portion 31 will be described in more detail. As shown in FIG. 2, the distal end portion 31 of the wire main body 30 is formed into a smooth curved surface by a top portion 32 that forms an extreme distal portion of the wire main body 30 and a surrounding portion 33 that makes the top portion 32 continuous with a peripheral surface 34 of the wire main body 30. In the exemplary embodiment, the distal end portion 31 is formed to have a hemispherical surface. However, a shape of the distal end portion 31 is not limited to a hemispherical shape but may be either a spherical shape or an aspherical rounded shape such that the peripheral surface 34 is continuous with the top portion 32.

A plurality of recesses are formed in the distal end portion 31 of the wire main body 30. One of the recesses is formed as a circular distal recess 35 in the top portion 32. Furthermore, a plurality of circular surrounding recesses 36 are formed in the surrounding portion 33. The plurality of surrounding recesses 36 are formed in a circumferential direction to form a row and a plurality of the rows are provided in an axial direction. In each row of the surrounding recesses 36 along the circumferential direction, the surrounding recesses 36 are identical in shape and disposed equidistantly in the circumferential direction. It is noted that being identical in shape signifies being identical in shape despite a difference in magnitude, e.g., size.

The surrounding recesses 36 differ in diameter in the axial direction. The surrounding recesses 36 are formed such that those closer to the top portion 32 have larger diameters and those closer to the peripheral surface 34 have smaller diameters. The surrounding recesses 36 closer to the peripheral surface 34 are disposed to be narrowly spaced in the circumferential direction, as compared with the surrounding recesses 36 closer to the top portion 32.

Figure 3:
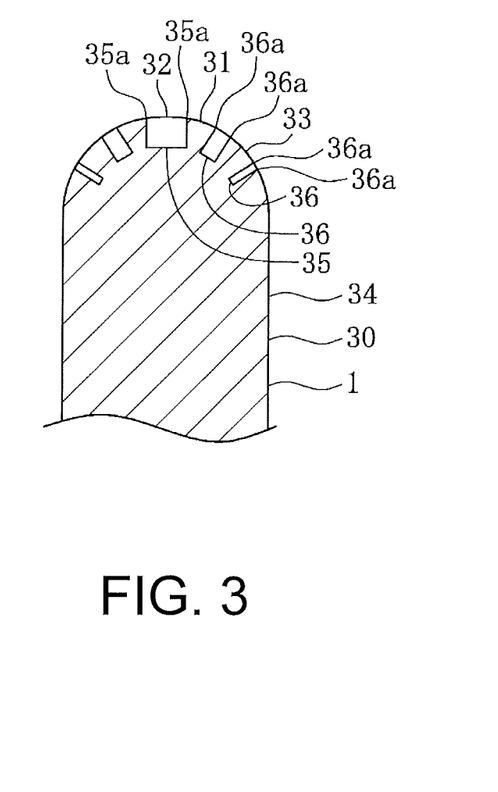
FIG. 3 is a cross-sectional view of the distal end portion of the guide wire according to the first exemplary embodiment of the disclosure.

As shown in FIG. 3, each of the distal recess 35 and the surrounding recesses 36 is formed to extend in a direction orthogonal to a direction of being tangential to a central position of each recess with the diameter kept unchanged.

That is, the distal recess 35 and the surrounding recesses 36 within the guide wire 1 are all columnar. Moreover, each of the recesses is formed as a recess which has the same depth and which is circular in a view from the direction orthogonal to the direction of being tangential to the central position of each recesses. An edge 35a is formed in an edge portion of the distal recess 35 along the circumferential direction while an edge 36a is similarly formed in an edge portion of each surrounding recess 36 along the circumferential direction.

Figure 4:
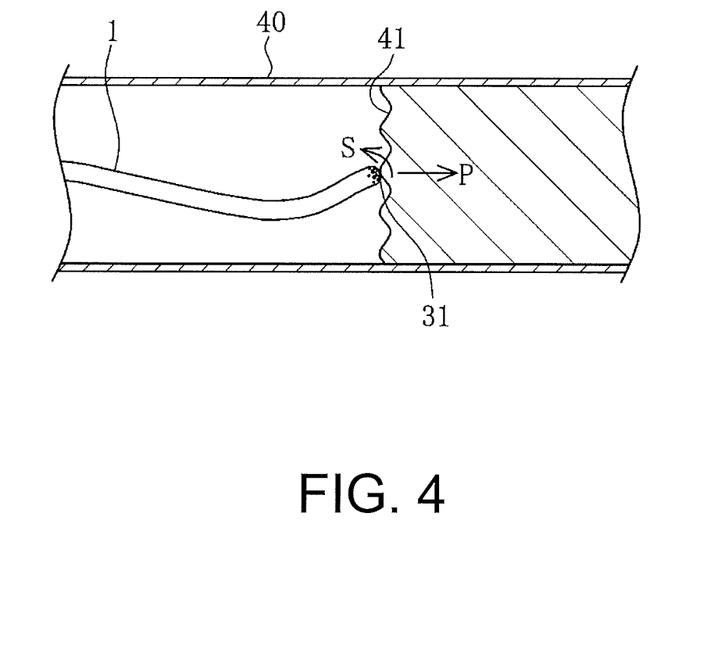
FIG. 4 is a pattern diagram of the guide wire, the distal end portion of which is attached to a stenosis of a blood vessel.

Since the distal end portion 31 of the guide wire 1 having the distal recess 35 and the surrounding recesses 36 is formed into the curved shape, the guide wire 1 is allowed to move forward smoothly without surface-contact of the distal end portion 31 with a blood vessel wall and the like. On the other hand, as shown in FIG. 4, in a case where an interior of a blood vessel 40 is fully blocked by a stenosis 41, the curved distal end portion 31 of the guide wire 1 may slip, for example, in an S direction in FIG. 4, when striking against a surface of the stenosis 41. To address this slipping, the distal recess 35 and the surrounding recesses 36 are formed in the distal end portion 31 of the guide wire 1, whereby the edges 35a and 36a of those recesses 35 and 36 are caught on the surface of the stenosis 41 to suppress slipping of the distal end portion 31. It is thereby possible to cause the guide wire 1 to move forward in a P direction which is a direction of forward movement in FIG. 4. That is, it is possible to improve penetrability of the guide wire 1 for penetrating the stenosis 41 while maintaining excellent passing performance of the guide wire 1.

Moreover, when a high lubricity coating is applied onto the distal end portion 31 of the guide wire 1 for improving the passing performance, the distal end portion 31 becomes particularly slippery. Therefore, it is possible to more effectively suppress the slipping of the distal end portion 31 on the stenosis 41 by forming the recesses in the distal end portion 31.

Even when the stenosis 41 does not completely block the blood vessel 40 as shown in FIG. 4, it is often difficult for the guide wire 1 to move forward into the stenosis 41. Even in that case, similar to the above, it is possible to achieve the effect of improving the penetrability according to the disclosure herein.

A direction in which the distal end portion 31 of the guide wire 1 slips varies, depending on an orientation of the guide wire 1, a surface state of the stenosis 41, a direction of a force acting on the guide wire 1 or the like, and thus, the distal end portion 31 is likely to slip in any given direction. To address this slipping, the surrounding recesses 36 are disposed equidistantly in the circumferential direction, so that it is possible to suppress the slipping of the distal end portion 31 of the guide wire 1 in any given direction.

Furthermore, each recess is formed to extend in the direction orthogonal to the direction of being tangential to the central position of the recess. Therefore, the edges 35a and 36a are caught on the surface of the stenosis 41 in the same way in any given direction when each recess comes in contact with the stenosis 41. It is, therefore, possible to exhibit a sufficient slipping suppressing effect in any given direction.

The disposition of the distal recess 35 and the surrounding recesses, recess diameters, the numbers, and depths can be set as appropriate and are not limited to specific ones. Preferably, however, the recess diameters are in a range from 0.01 to 0.3 mm, the number of the recesses is one in the top portion 32 and two to five rows of five to ten surrounding recesses in the surrounding portion 33, and the depths are in a range from 0.01 to 0.2 mm.

Various methods may be conceivable as a manufacturing method for forming the distal recess 35 and the surrounding recesses 36 in the distal end portion 31. For example, the distal recess 35 and the surrounding recesses 36 can be formed by drilling recesses in the distal end portion 31 of the wire main body 30 by means of a fine drill. Alternatively, a method may be conceivable for forming recesses by locally applying a heat to a surface of the distal end portion 31. As for the distal recess 35, at a time of working the distal end portion 31 of the wire main body 30 into the curved shape by a rotary grindstone, a protruding portion is formed on the grindstone and the distal recess 35 can be formed by this protruding portion. In another alternative, a method may be conceivable for forming recesses by means of a die having an opposite shape to the shape of the distal end portion 31.

Figure 5:
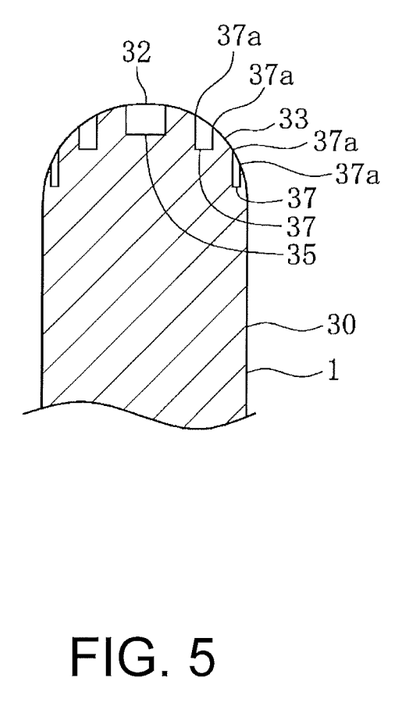
FIG. 5 is a cross-sectional view of a distal end portion of a guide wire according to a second exemplary embodiment of the disclosure.

In the exemplary embodiment, each of the recesses is formed to extend from the surface of the distal end portion 31 in a perpendicular direction as shown in FIG. 3. Alternatively, as shown in a second exemplary embodiment in FIG. 5, each of surrounding recesses 37 may be formed to extend in a direction from the distal side to the proximal side of the guide wire 1 (axial direction of the guide wire 1). In this case, an angle of an edge 37a of each surrounding recess 37 varies along the circumferential direction, so that there occurs a difference in effect depending on a slipping direction of the guide wire 1 but it is possible to attain the effect of improving the penetrability for penetrating the stenosis 41.

Figure 6:
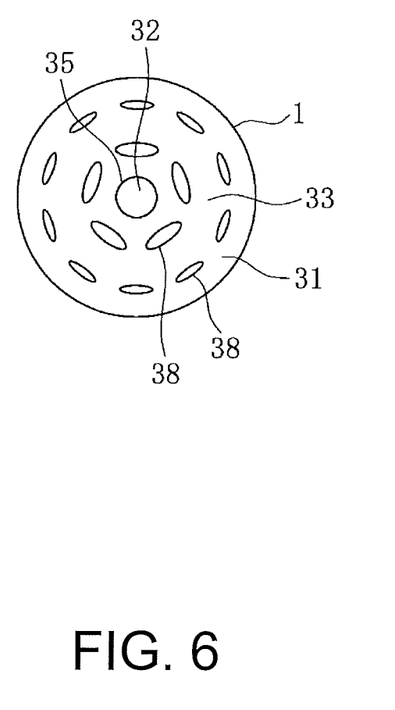
FIG. 6 is a front view of a distal end portion of a guide wire according to a third exemplary embodiment of the disclosure.

Other embodiments of the surrounding recesses will be described. As shown in FIG. 6, surrounding recesses 38 may be each formed into an oval shape in a third exemplary embodiment. In this case, the shape of each surrounding recess 38 within the guide wire 1 is an oval cylindrical shape. It is noted that the shape of the distal end portion 31 and that of the distal recess 35 in this embodiment are similar to those in the first embodiment.

The surrounding recesses 38 according to the third exemplary embodiment are each disposed such that a long axis faces along the circumferential direction of the surrounding portion 33 and a short axis faces along the axial direction of the surrounding portion 33. A force acts on the guide wire 1 for inserting the guide wire 1 in the axial direction, so that the distal end portion 31 slips on the stenosis 41 along the curved shape of the distal end portion 31 in the axial direction. Each surrounding recess 38 according to the third exemplary embodiment is elongated in the direction orthogonal to the axial direction and the distal end portion 31 is caught on the stenosis 41 by a large length when the distal end portion 31 slips in the axial direction. Therefore, it is possible to increase the resistance force against the slipping.

Figure 7:
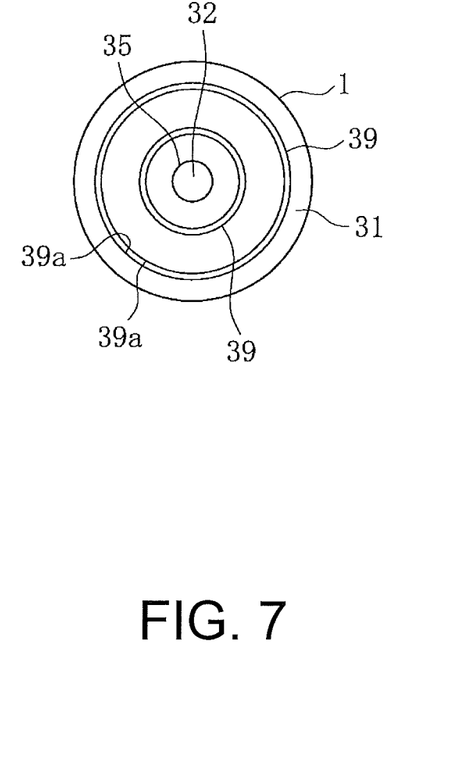
FIG. 7 is a front view of a distal end portion of a guide wire according to a fourth exemplary embodiment of the disclosure.

Moreover, as shown in a fourth exemplary embodiment in FIG. 7, surrounding recesses 39 may be formed into a groove shape concentric with the distal recess 35. In this case, edges 39a are coupled together throughout an entire circumference. Owing to this, even when the distal end portion 31 slips at any given angle, it is possible to generate a resistance force to ensure that the edges 39a are caught on the stenosis 41 and to suppress slipping.

As described so far, the guide wire 1 according to the exemplary embodiments includes the wire main body 30 formed into the linear shape, the distal end portion 31 of the wire main body 30 is formed into the curved shape by the top portion 32 that forms the extreme distal portion and the surrounding portion 33 that makes the top portion 32 continuous with the peripheral surface 34 of the wire main body 30, and the plurality of recesses 35 and 36 are formed in the distal end portion 31. With this configuration, it is possible to suppress the slipping of the distal end portion 31 on the stenosis 41 by the recesses 35 and 36 and improve the penetrability of the guide wire 1 while improving the passing performance of the guide wire 1 within the body lumen by the curved distal end portion 31.

Moreover, forming the recesses 35 and 36 in the top portion 32 and the surrounding portion 33, respectively can suppress the slipping even when the distal end portion 31 of the guide wire 1 does not move straight into the stenosis 41.

Furthermore, forming the recesses 36 along the circumferential direction of the surrounding portion 33 can suppress the slipping on the stenosis 41 irrespective of the circumferential orientation of the guide wire 1.

Moreover, making the recesses 36 formed in the surrounding portion 33 identical in shape and disposing the recesses equidistantly along the circumferential direction can constantly suppress the slipping on the stenosis 41 irrespective of the circumferential orientation of the guide wire 1.

Furthermore, forming a plurality of rows of the recesses 36 along the axial direction of the surrounding portion 33 can suppress the slipping of the distal end portion 31 on the stenosis 41 in a wider range.

Further, forming the circular distal recess 35 in the top portion 32 and forming the circular or oval surrounding recesses 36 in the surrounding portion 33 can ensure suppression of the slipping because the edge 35a or 36a of the distal recess 35 or each surrounding recess 36 is caught on the stenosis 41 at any given angle where the guide wire 1 comes in contact with the stenosis 41.

Moreover, configuring the surrounding recess 38 to be oval and disposing the surrounding recess 38 such that the long axis faces along the circumferential direction of the surrounding portion 33 and the short axis faces along the axial direction of the surrounding portion 33 can elongate the edge of each surrounding recess 38 in the direction orthogonal to a slipping direction and increase the resistance force against the slipping when the distal end portion 31 of the guide wire 1 slips against an axial force.

While the shape of the distal recess 35 is the circular shape and the shape of each surrounding recess is the circular shape, the oval shape, or the groove shape in the abovementioned exemplary embodiments, the shapes may be the other shapes. For example, the shapes may be a polygonal shape or may be a shape such as a star shape or a crisscross shape.

Nevertheless, the distal recess 35 faces the direction of forward movement of the guide wire 1 and the edge 35a needs to receive the slipping of the distal end portion 31 from any direction when the slipping of the distal end portion 31 on the stenosis 41 occurs. Preferably, therefore, the distal recess 35 has a circular shape that enables the edge 35a to face in the same way at any angle.

Moreover, the shapes of the distal recess 35 and the surrounding recesses within the guide wire 1 are the columnar shape or the oval cylindrical shape according to the above-exemplary embodiments, but the shapes may be the other shapes such as the spherical shape or a hemispherical shape having an aspherical surface.

Furthermore, in the above-mentioned exemplary embodiments, the distal recess 35 is formed in the top portion 32 of the distal end portion 31 of the wire main body 30 and the surrounding recesses are formed in the surrounding portion 33. However, it suffices to form a plurality of recesses at least in the distal end portion 31 and the plurality of recesses may be disposed arbitrarily without limitation.

Moreover, while the catheter 10 using the guide wire 1 according to the above-mentioned exemplary embodiments is an over-the-wire type, the catheter 10 may be a rapid-exchange type. Furthermore, an object using the guide wire 1 is not limited to the catheter but may be an endoscope or the like.

The detailed description above describes features and aspects of exemplary embodiments of a guide wire. The invention is not limited, however, to the precise embodiment and modifications described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A guide wire comprising:
a wire main body having a solid core wire and a linear shape,
wherein a distal end portion of the wire main body includes a top portion and a surrounding portion, the top portion having a curved shape that defines an extreme distal tip and the surrounding portion extending from the top portion such that the top portion is continuous with a peripheral surface of the wire main body, and
a plurality of recesses defined in the curved shape defining the extreme distal tip.

2. The guide wire according to claim 1, wherein the plurality of recesses are defined in the top portion and the surrounding portion, respectively.

3. The guide wire according to claim 2, wherein the plurality of recesses are defined along a circumferential direction of the surrounding portion.

4. The guide wire according to claim 3, wherein the plurality of recesses defined in the surrounding portion are identical in shape and disposed equidistantly along the circumferential direction.

5. The guide wire according to claim 3, wherein the plurality of recesses are arranged to form a plurality of rows along an axial direction of the surrounding portion.

6. The guide wire according to claim 5, wherein the plurality of rows includes two to five rows, each of said plurality of rows including five to ten of the plurality of recesses.

7. The guide wire according to claim 5, wherein one of the plurality of rows is disposed closer to the top portion and an other one of the plurality of rows is disposed closer to the peripheral surface, the plurality of recesses in the one of the plurality of rows disposed closer to the top portion having larger diameters than the plurality of recesses in the other one of the plurality of rows disposed closer to the peripheral surface.

8. The guide wire according to claim 1, wherein the plurality of recesses includes a circular distal recess disposed in the top portion and at least one circular or oval surrounding recess disposed in the surrounding portion.

9. The guide wire according to claim 8, wherein the at least one surrounding recess is oval and disposed such that a long axis faces along a circumferential direction of the surrounding portion and a short axis faces along an axial direction of the surrounding portion.

10. The guide wire according to claim 8, wherein the distal recess and the at least one surrounding recess extend in an orthogonal direction relative to a tangent of a central position of the distal recess and the at least one surrounding recess, respectively.

11. The guide wire according to claim 8, wherein the distal recess and the at least one surrounding recess extend in an axial direction of the guide wire.

12. The guide wire according to claim 1, wherein the plurality of recesses are columnar.

13. The guide wire according to claim 12, wherein a depth of the plurality of recesses is in a range from 0.01 to 0.2 mm.

14. The guide wire according to claim 12, wherein each of the plurality of recesses defines an edge portion along a circumferential direction.

15. The guide wire according to claim 1, wherein the plurality of recesses includes one distal recess in the top portion and a plurality of said plurality of recesses in the surrounding portion.

16. A guide wire comprising;
a wire main body having a linear shape,
wherein a distal end portion of the wire main body defines a top portion and a surrounding portion, the top portion having a curved shape defining a distalmost tip and the surrounding portion extending from the top portion such that the curved surface is continuous with a peripheral, circumferential surface of the wire main body, and
a plurality of recesses defined in the curved surface of the distalmost tip.

17. The guide wire according to claim 16, wherein the plurality of recesses are defined in the top portion and the surrounding portion, respectively.

* * * * *